United States Patent
Kenten et al.

(10) Patent No.: US 6,174,709 B1
(45) Date of Patent: *Jan. 16, 2001

(54) METHOD FOR MAKING A PRIMER AND NUCLEIC ACID EXPONENTIAL AMPLIFICATION METHODS USING SAID PRIMER

(75) Inventors: John H. Kenten, Gaithersburg, MD (US); John R. Link, Springfield, VA (US)

(73) Assignee: IGEN International, Inc., Gaithersburg, MD (US)

( * ) Notice: Under 35 U.S.C. 154(b), the term of this patent shall be extended for 0 days.

This patent is subject to a terminal disclaimer.

(21) Appl. No.: 08/221,543

(22) Filed: Jan. 31, 1994

Related U.S. Application Data

(63) Continuation of application No. 07/804,951, filed on Dec. 11, 1991, now abandoned.

(51) Int. Cl.[7] ............................... C12Q 1/68; C12P 19/34
(52) U.S. Cl. ........................ 435/91.2; 435/6; 435/91.1; 536/25.3
(58) Field of Search ............................ 435/6, 91.1, 91.2, 435/810; 436/501; 536/22.1, 23.1, 24.1, 24.3, 24.33, 25.3; 935/77, 78, 88

(56) References Cited

U.S. PATENT DOCUMENTS 5,043,272 * 8/1991 Hartley .................................. 435/91
5,413,909 * 5/1995 Bassom et al. ........................ 435/6
5,508,178 * 4/1996 Rose et al. ........................ 435/91.1

FOREIGN PATENT DOCUMENTS 0 379 369 A3   7/1990  (EP) .

OTHER PUBLICATIONS

Kalma, et al. Polymerase Chain Reaction (PCR) Amplification with a Single Specific Primer. Biochem. Biophys. Res. Comm (1990) 167:504–506.*

* cited by examiner

*Primary Examiner*—Ardin H. Marschel
(74) *Attorney, Agent, or Firm*—Kramer Levin Naftalis & Franklin LLP; Barry Evans

(57) ABSTRACT

A process for exponentially amplifying a selected nucleic acid sequence present in a sample, comprising the steps of forming a mixture of the sample and a single primer designed to hybridize with the selected nucleic acid sequence; causing the single primer to hybridize to a single strand of the nucleic acid sequence of interest; forming a duplex product of the nucleic acid by a polymerase reaction; separating the duplex product into single strands; and repeating the preceding steps until the rate of production of the amplification product is exponential and the nucleic acid sequence of interest has been amplified.

25 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:1:

CTCCACACTC TTTTGGATGC TCTGGTCATC      30

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:2:

CACATCATCC TCTGTTTGTG CTCTTTCCT      29

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:3:

CAGTTAATAC ACCTAATTAA CAAATCACAC      30

(2) INFORMATION FOR SEQ ID NO:4:

```
        (i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:4:

ACAACATTAG AACAGCAATA CAACAAACCG                                        30

(2) INFORMATION FOR SEQ ID NO:5:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:5:

CACCGCAGGC ACCTTATTAA TAAATTGTAT                                        30

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:6:

GACACATTGG AAAAACTAAC TAACACTGGG                                        30

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:7:

GCCACGCAAG CGGGTGAGGA GTTCC                                             25

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:8:

GTCCGAGGCA AATGCCAATA ATGG                                              24
```

METHOD FOR MAKING A PRIMER AND NUCLEIC ACID EXPONENTIAL AMPLIFICATION METHODS USING SAID PRIMER

This application is a continuation of U.S. application Ser. No. 07/804,951 filed Dec. 11, 1991, now abandoned.

FIELD OF THE INVENTION

This invention relates to exponential amplification of nucleic acid sequences achieved by use of a specific single unpaired primer.

Several publications are referenced in this application by arabic numerals in parentheses. Full citation of these references is found at the end of the specification immediately preceding the claims. These references describe the state-of-the-art to which this invention pertains.

BACKGROUND OF THE INVENTION

It is well known that a nucleic acid such as deoxyribonucleic acid (DNA) is able to serve as its own template during self-replication. It is also well known that a double stranded or duplex nucleic acid can be separated into its component single strands. These properties have been exploited to permit the in vitro amplification and modification of nucleic acid sequences by the polymerase chain reaction (PCR) (also referred to herein as two-primer amplification).

PCR is an in vitro, enzyme-based replication of nucleic acid sequences, using two oligonucleotide primers designed to hybridize to opposite strands and flank the region of interest on the target polynucleotide sequence. During repetitive cycles the nucleic acid is subjected to strand separation, typically by thermal denaturation, the primers are hybridized (by annealing if thermal cycling is used) to the single strand templates, and an enzyme such as DNA polymerase (DNA template to DNA primer extension) or reverse transcriptase (ribonucleic acid or "RNA" template to DNA primer extension or DNA template to DNA primer extension) extends the primers on the templates. Both of the strands (plus and minus), including newly synthesized strands, are made available as templates for the extension of both primers respectively by the strand separation step. The result, with two primers, is an exponential increase (hence the term "chain reaction") in template nucleic acid copy number (both plus and minus strands) with each cycle, because with each cycle both the plus and minus chains are replicated (1, 2). The nucleic acid duplex which results will have termini corresponding to the ends of the specific primers used. It is possible, by means of PCR, to amplify, detect, or otherwise modify a nucleic acid sequence in vitro (1, 2).

The art teaches that if a single unpaired primer is used in place of two (paired) primers, the result is a linear growth in extension product copy number instead of an exponential growth of both strands (3). It is generally believed that the reason for the linear growth in copy number with cycle number using a single unpaired primer is that only the template strand is replicated during each cycle. The primer extension itself is not copied.

The linear growth in copy number with a single primer was confirmed by Kim et al. (3). Kim et al. developed a recombinant fragment assay based on PCR amplification. A pair of primers were prepared which were each complementary to the opposite terminals of the recombinant sequence expected to be formed from two parent chromosomal sequences. Each of the two parent chromosomal sequences was complementary to only one of the primers. As predicted, only the recombinant sequence (having binding sites for both primers) was detected by Kim et al. after 50 cycles. Thus, this assay provides a strong confirmation for the previous observations in the art literature (1,2,3,4) that two primers are required for exponential amplification.

Single primer amplification has been used to perform "cycle sequencing" in a process marketed by Applied Biosystems, Inc. (San Jose, Calif.). Cycle sequencing relies upon a single, dye labeled primer or terminator to achieve linear amplification of the extension products. The primer extension products are then collected and sequenced in order to derive the sequence of the original DNA template. This technique is reported to be particularly advantageous in allowing sequencing of large constructs with minimal sample size (e.g. 42 kb construct using only 1.2 μg of sample) (5). However, the amplification achieved during cycle sequencing is described as different from PCR because "PCR uses two different primers to achieve exponential amplification of the template . . . . Cycle sequencing, on the other hand, uses only one primer to achieve linear amplification of the extension products." (5).

Single-primer linear amplification has also proved useful as a technique for detecting DNA methylation and protein-DNA interactions by providing "selective, linear amplification by thermostable DNA polymerase from *Thermus aquaticus*" (taq DNA polymerase) (6). Thus, single-primer amplification is used by the art in certain specialized procedures to provide the expected linear amplification.

The preparation of primers for PCR requires that the terminal sequences of the nucleic acid strands (both the plus and minus templates) to be amplified or detected, be known (2). The sequence information may be derived by direct sequencing of the terminals of the nucleic acid of interest, or by sequencing the terminal of a polypeptide and producing a corresponding copy oligonucleotide primer. The optimal primer size is typically about 20–30 bases in length (2), but workable primers may be smaller or larger in particular circumstances. As is well known, as primer size decreases, the likelihood that the primer will hybridize to an unplanned site on the sequence of interest increases. Unplanned hybridizations can lead to an interruption of amplification of the desired product and production of products having either a smaller size or an undesired primer insert. Thus, the selection of two optimal primers for PCR requires the avoidance of unplanned hybridization with the sequence of interest whenever practicable.

The rational selection of primer sequence to avoid unplanned hybridizations is well known. Algorithms are known by which the artisan may compare proposed primer sequences to the entire template sequence (where known) and to any other sequences which are known to be present in an assay mixture. Such algorithms are typically implemented by means of a programmable digital computer able to store sequences for comparison, execute a programmed comparison of all sequences, and thereby estimate the likelihood of a desired or an unplanned hybridization occurring based upon a determination of relative percent complementarities and other factors known to affect the likelihood of hybridization (e.g. stringency conditions).

The necessity for determining the terminal portion of the opposite strands of a nucleic acid sequence of interest and preparing two primers hybridizable thereto may be avoided by means of a kit marketed by Clontech Laboratories of Palo Alto, California (7). The Clontech UNI-AMPTM Adaptor (Cat. No. 5991-1, 5992-1, 5993-1, 5994-1 or 5995-1) is ligated onto blunt-ended DNA or cDNA of interest. A single, complementary UNI-AMP™ primer (Cat. No. 5990-1) is then used to amplify the DNA by the standard PCR process. Thus, by means of an attachable pre-prepared oligonucleotide adaptor, and a pre- prepared primer complementary to the adaptor, the equivalent of a conventional PCR may be performed using only one primer sequence and without any need to analyze the terminal sequences and prepare two primers. However, this method provides no specificity for the amplification. All DNA sequences present will receive a universal primer binding site and be amplified or detected by the universal primer. Thus, the universal nature of this method lacks the specificity inherent in methods which provide for specific primers designed to be complementary to a portion of the DNA sequence of interest.

Most recently, Caetan-Anolles et al. have reported DNA amplification fingerprinting using very short arbitrary primers (7). By reducing the primer size to a range of five to nine bases, Caetan-Anolles et al. were able to relax the stringency of the polymerase reaction. A characteristic spectrum of short DNA products of varying complexity was produced with 30–40 thermal cycles. The reported mechanism was priming at multiple, unspecified priming sites on each DNA target sequence. The major disadvantages of this reported single primer system are its complete lack of specificity and the consequent mixture of short amplification products. The Caetan-Anolles et al. assay does not possess the advantages of a method for single primer amplification which is specific for target nucleic acid sequences of interest. The requirement for two primers, each complementary to an opposite terminal of a polynucleotide sequence of interest, to achieve the exponential amplification of PCR represents a relative disadvantage to the artisan seeking a lower cost, simple and rapid method of practicing in vitro amplification of nucleic acid at an exponential rate. The disadvantages of two-primer PCR include the necessity of preparing two oligonucleotide primers, and, as described above, the necessity of confirming that the paired primers do not participate in unplanned hybridizations, including avoiding complementarity between the two primers (especially at the 3' end) to prevent them from linking and forming a template able to overwhelm the reaction by replicating primer dimers (resulting in an artifact which can seriously interfere with PCR results) (8). There is another potential source of the primer dimer artifact. The tag DNA polymerase and certain other polymerases have been shown to have a weak non-template directed activity which can attach bases to a blunt-ended duplex (8,9). It has been hypothesized that if this non-template directed activity were to occur on a single-stranded oligonucleotide, there is a good chance that the extension would form a short 3' overlap with the other primer which could promote dimerization (8). When primer dimers have been analyzed, they have been found to be composed of both primers. Thus, one way to avoid primer dimerization would be to use only a single unpaired primer.

Two-primer amplification has been used to isolate new gene sequences from a polynucleotide sequence library. However, the requirement for primers complementary to the sequences of the opposite termini of both strands of the new gene sequence has represented a real obstacle to the use of polymerase amplification for this purpose. of course it is well known that a new gene may be isolated by means of a sufficiently complementary probe incorporating a portion of the sequence of the new gene, but probe isolation methods lack the sensitivity provided by PCR.

A similar limitation exists in the practice of PCR to provide amplification of multiple nucleic acid sequences of interest present in the same sample. In addition, as the number of primers present in an amplification mixture increases, the efforts required to avoid unplanned hybridization between each primer and the nucleic acid sequence of interest (target sequences), or between two or more primers (e.g. resulting in primer dimer artifacts), greatly increases.

Thus, it can be appreciated that a heretofore unavailable method for achieving exponential amplification of a specific nucleic acid sequence of interest requiring only a single primer but retaining specificity of action would be an important and unexpected contribution to the art.

OBJECTS OF THE INVENTION

It is a primary object of the invention to provide a process for exponentially amplifying a nucleic acid sequence of interest present in a sample using a single primer designed to hybridize with the nucleic acid sequence of interest.

It is another and related object of the invention to provide a method for making a primer for single primer exponential amplification of a nucleic acid sequence of interest.

It is yet another and related object of the invention to provide a method for exponential amplification of a nucleic acid sequence of interest without the necessity for preparing two primers.

It is a further and related object of the invention to provide a method for exponential amplification of a nucleic acid sequence of interest which avoids the formation of interfering primer dimer artifacts between paired primers.

It is yet a further and related object of the invention to provide a method for exponential amplification of multiple nucleic acid sequences of interest without the necessity of providing multiple pairs of compatible primers.

SUMMARY OF THE INVENTION

The invention is in a process for exponentially amplifying a nucleic acid sequence of interest present in a sample. The process comprises forming a mixture of the sample and a single primer designed to hybridize with a strand of said nucleic acid sequence of interest; causing the single primer to hybridize with a single strand of said nucleic acid sequence of interest; forming a duplex product of the said strand by a polymerase reaction; separating the duplex product into single strands; and repeating the preceding three steps until the rate of production of the duplex product is exponential and the nucleic acid sequence of interest has been amplified.

The amplifications performed by the methods of the invention are approximately linear until about thirty to sixty cycles are completed. Thereafter, significant exponential amplification is observed. The cycle number when significant exponential amplification begins will vary with the template, the primer and other reaction conditions. Thus, for each amplification (for each primer/template combination) according to the invention, successful amplification will usually be achieved by assaying the production of product as a function of cycle number, in addition to the optimization of the other factors well known to the art.

Surprisingly, it has now been found that a single primer designed to hybridize with a nucleic acid sequence of interest is able to provide exponential amplification of the nucleic acid sequence of interest. Exponential amplification commences after about thirty to sixty amplification cycles. The exponential amplification proceeds without the necessity of preparing two primers, and the formation of primer dimer artifacts are avoided. The unexpected exponential amplification of the invention greatly simplifies the process of amplifying multiple nucleic acid sequences of interest present in a sample.

The invention makes it possible to detect the presence of a nucleic acid sample of interest in a sample by incorporating a labeled primer followed by measurement of the labeled modification product. Any accurate and sensitive assay method for detection or quantification of amplification products may be used to evaluate empirically the optimum parameters for single primer amplification or to detect the amplification product of a single primer amplification. A preferred assay method known to the art relies upon the incorporation of primers labeled by electrochemiluminescent (ECL) tags. An ECL tag is prepared and linked to single oligodeoxynucleotide primers of the invention. The oligodeoxynucleotide primers are each prepared to be sufficiently complementary to a different nucleic acid sequence of interest. Primers are labeled via an amino group introduced during synthesis, or directly during synthesis, using tag NHS and tag phosphoramidite respectively.

Oligonucleotide probes may also be prepared which are complementary to the amplification products of specific oligonucleotide primers. These oligonucleotide probes are synthesized to be sufficiently complementary to the region encompassed by the first 20–50 bases of the template nucleic acid strand which is copied by the primer. The probes are linked to a biotin moiety via an amino group introduced during synthesis.

The amplification products in accordance with the invention are mixed with the oligonucleotide probe and allowed to hybridize. The complex formed from the hybridization of the probe with the amplified and labeled target sequence is captured by streptavidin coated beads. The streptavidin coated magnetic beads bearing the amplification product and probe complex are then analyzed for ECL signal levels by means of an apparatus, described below, which is (10) able to induce and measure electrochemiluminescence. The presence and quantity of the ECL tag incorporated in the amplification product is read and accurately determined.

In yet a further embodiment, the invention is in a method for making a primer for single primer exponential amplification of a nucleic acid sequence of interest having a 3' terminal and a 5' terminal. A putative primer of approximately 10–40 base pairs designed to hybridize to a first primer site located approximately at the 3' terminal of the nucleic acid sequence of interest is prepared.

The sequence of the putative primer is then compared to sequences 5' of the primer selection site to identify complementary region(s) of the nucleic acid sequence of interest. If such complementary region(s) are identified it may be expected that they will serve as second insertion sites and the operability of the putative primer may be expected. The 5' sequences of said nucleic acid sequence of interest are located within 5 kb of said primer selection site and preferably within 2 kb of said primer selection site. The complementarity may be in the range of 7.5 to 100% and is preferably in the range of 30 to 100%. Thus, the lower limit of complementarity by this method is in the range of 7.5 to 30%. The putative primer may then be used in the method of the invention to confirm its operability.

If the aforedescribed comparison method fails to provide single primer exponential amplification by the putative primer, a second putative primer can be obtained by frame shifting the first primer selection site one base towards the 5' terminal of the nucleic acid of interest and preparing a second putative primer of approximately 10–40 base pairs designed to hybridize to the shifted primer site. The comparison process may be repeated to determine the likelihood of success with the second putative primer. By shifting the primer site one more base towards the 5' terminal of said nucleic acid of interest a third putative primer of approximately 10–40 base pairs designed to hybridize to a third shifted primer site may be prepared. The process may be continued to provide a series of putative priming sites and a series of putative primers designed to hybridize thereto. The successful primer is ultimately determined by screening the series of frame-shifted putative primers to identify a single primer which is operative for single primer exponential amplification.

In a further aspect, a modified single primer may be prepared from a putative first, second . . . or $n^{th}$ primer by changing a first non-complementary base of the putative primer, at or near the 3' terminal of the putative primer, to be complementary to a corresponding base of a second primer insertion site. This step may be repeated by changing a second non-complementary base located 5' of and approximately adjacent to the first changed base to produce a second modified putative primer. These steps may be repeated for each non-complementary base in the 5' direction to generate a series of modified putative primers having an increasing complementarity to the second primer insertion site and having decreasing complementarity to the first primer insertion site. An operative primer is selected by screening the series of modified putative primers to determine which is operative for single primer exponential amplification.

DETAILED DESCRIPTION OF THE INVENTION

Definitions

In order to more clearly understand the invention, certain terms are defined as follows.

A "nucleotide" is one of four bases: adenine, cytosine, guanine, and thymine (DNA) or uracil (RNA), plus a sugar (deoxyribose for DNA, ribose for RNA), plus a phosphate. In order to provide monomers for the DNA polymerization reaction, typically all four of the deoxynucleotide triphosphates are required. A nucleotide as defined herein may also include modified bases such as 5-methyl-dCTP and 7-deaza-dGTP used to improve the action of polymerase on templates. The term nucleotide as used herein also includes bases linked to biotin and digoxigenin (Digoxigenin-11-UTP from Boehringer Mannheim, Indianapolis, Indiana), and biotin-21-UTP and amino-7-dUTP (Clontech, Palo Alto, Calif.) which may be incorporated directly into a primer or into a primer extension product during amplification, to provide for selective binding of amplified sequences.

An "oligonucleotide" is a sequence formed of at least two nucleotides.

A "polynucleotide" is a long oligonucleotide and may be either RNA or DNA.

While the term oligonucleotide is generally used in the art to denote smaller nucleic acid chains, and "polynucleotide" is generally used in the art to denote larger nucleic acid chains including DNA or RNA chromosomes or fragments thereof, the use of one or the other term herein is not a limitation or description of size unless expressly stated to be.

It is also well known to the art that the term "nucleic acid" refers to a polynucleotide of any length, including DNA or RNA chromosomes or fragments thereof with or without modified bases as described above.

A "sequence" (e.g. sequence, genetic sequence, polynucleotide sequence, nucleic acid sequence) refers to the actual enumerated bases (ribose or deoxyribose) present in a polynucleotide strand reading from the 5' to 3' direction.

A "specific or selected" nucleotide sequence refers to a particular sequence distinguishable (i.e., by hybridization analysis) from other different sequences (e.g., the specific nucleotide sequence 5'-ATGCCC-3' is not the same sequence as 5'-AAGCCC-3').

The "complement" to a first nucleotide sequence is well known to be a second sequence comprising those bases which will pair by Watson-Crick hybridization with the first sequence. Thus, the complement to the deoxyribonucleic acid (DNA) sequence 5'-ATGC 3' is well known to be 5'-GCAT 3'. For duplex, or double stranded DNA, each of the two strands are described as complementary to the other or as a complementary pair. The terms complement and anticomplement may also be used. With reference to the identification of the strand of duplex DNA from which transcription to RNA proceeds, the transcription strand is generally described as plus and its complement as minus (or "+" and "−"), or the transcription strand may be described as the sense strand, and its complement as antisense. Two strands each hybridized to the other having all base pairs complementary, are 100% complementary to each other. Two strands, each hybridized to the other, having 5% of bases non-complementary, are 95% complementary (or the two strands have 95% complementarity).

"Homology" between polynucleotide sequences refers to the degree of sequence similarity between the respective sequences. Two strands which are identical in sequence have 100% sequence homology. Two strands which differ by 5% of sequences have 95% sequence homology. The greater the degree of homology between two strands A and B, the greater the complementarity between A and the complement of B.

A "probe" is a single or double stranded nucleic acid which has a sequence complementary to a target nucleic acid sequence of interest and which has some additional feature enabling the detection of the probe—target duplex. The artisan will understand that if the probe and/or the target is double stranded, the double stranded nucleic acid must undergo strand separation before hybridization can take place.

A probe is rendered detectable by an attached tag or marker. A tag or marker linked to a probe may include a fluorescent or luminescent tag, an isotopic (e.g. radioisotope or magnetic resonance) label, a dye marker, an enzyme marker, an antigenic determinant detectable by an antibody, or a binding moiety such as biotin enabling yet another indicator moiety such as a streptavidin coated bead to specifically attach to the probe. When the labeled or tagged probe - target duplex is formed, that duplex may be detected by the characteristic properties of the tag or label. Alternatively, as described for the ECL assays in the following examples, the probe with its binding moiety allows the capture of labeled target, via hybridization and duplex formation, allowing detection by a label or other art known means.

The term "label" or "labeled" when applied to a nucleic acid means that the nucleic acid in question is linked to a moiety which is detectable by its properties which may include: luminescence, catalysis of an identifying chemical substrate, radioactivity, or specific binding properties. Thus, the term "label" includes ligand moieties unless specifically stated otherwise.

A "template" is any sequence of nucleic acid upon which a complementary copy is synthesized. This may in general be DNA to DNA replication, DNA to RNA transcription, or RNA to DNA reverse transcription. A DNA template provides the sequence information for extension of the complementary primer by the DNA polymerase reaction. An RNA template may provide the sequence information for extension of a complementary DNA primer by an analogous reaction catalyzed by the enzyme reverse transcriptase. As is well known to the art, the template may be found in a single or double stranded form. If the template enters the amplification process in the double stranded form, the template strand will not hybridize to its complementary primer until it is denatured by the first thermal denaturing cycle. If the template enters the amplification process already in the single stranded form, the primer will hybridize (described as annealing when thermal cycling is utilized) with its complementary template before the first thermal denaturing step.

A "primer" is a relatively short segment of oligonucleotide which is complementary to a portion of the sequence of interest (the sequence of interest can be a subfragment within a larger nucleic acid sequence). A primer represents a 5' terminus of the resulting extension product. A primer which is complementary at its 3' terminus to the sequence of interest on the template strand enables this 3' terminus to be acted on by a polymerase on hybridization to the template. It is well known that modifications to the 3' end will affect the ability of an oligonucleotide to function as primer. An example is the incorporation of a dideoxynucleotide as in DNA sequencing thus preventing the action of DNA polymerases. It is well known that the length of the primer will depend upon the particular application, but that 20–30 base pairs is a common size. As is well known, a primer need not be a perfect complement for successful hybridization to take place. If the primer is an imperfect complement, an extension product will result which incorporates the primer sequence, and during a later cycle, the complement to the primer sequence will be incorporated into the template sequence. Thus, it is well known that a properly selected primer having a sequence altered from that of the complement of the template may be used to provide in vitro mutagenesis. The primer may incorporate any art known nucleic acid bases, including any art known modified or labeled bases as defined above so that the primer extension product will incorporate these features to permit separation and detection of the primer extension product. A tag or marker advantageously linked to a primer may include a fluorescent or luminescent tag, an isotopic (e.g. radioisotope or magnetic resonance) label, a dye marker, an enzyme marker, an antigenic determinant detectable by an antibody, or a binding moiety such as biotin enabling yet another indicator moiety such as a streptavidin coated bead to specifically attach to the primer or any nucleic acid sequence incorporating that primer. When the labeled or tagged amplification product is formed, that amplification product may be detected by the characteristic properties of the tag or label.

The term primer extension product describes the primer sequence together with the complement to the template produced during extension of the primer.

A specific or selected primer is one which is designed to hybridize with a particular template sequence to achieve the desired result by making the primer complementary or approximately complementary to the 3' terminal of the template sequence. The specific primer will selectively achieve the desired result even if the target template sequence is present in a mixture of many other nucleic acid sequences.

The specific or selected primer is distinguished from a "universal primer" which will indiscriminately anneal to any DNA sequence to which a complementary (to the primer)

adaptor terminal sequence has been attached. With a universal primer, care must be taken to isolate the nucleic acid of interest, or otherwise direct the ligation procedure only to the desired DNA sequence of interest, to avoid randomly attaching the adaptor to all nucleic acid sequences present.

The term "single primer" means a single, unpaired, specific or selected primer designed to selectively hybridize with a target nucleic acid sequence of interest. "Single primer amplification" is a method for amplifying a nucleic acid utilizing only a single, unpaired, primer which is complementary to a portion of the sequence of interest. There is no need for a second primer as is taught by the art to achieve exponential amplification of both a selected nucleic acid sequence of interest and its complement. A single primer amplification according to the invention exhibits approximately linear amplification during the early cycles, but after a variable number of cycles exponential amplification commences.

A "strand" is a single nucleic acid sequence. Thus, a duplex or double stranded chromosome, chromosome fragment or other nucleic acid sequence may be separated into complementary single strands.

"Strand separation" refers to the conversion of a double stranded or duplex nucleic acid to two complementary single stranded polynucleotides. The separation process may employ well known techniques including: enzyme mediated separation (e.g. by the enzyme helicase) (2), physical-chemical separation (pH, ionic concentration and the like), and thermal separation also known as thermal denaturing. Thermal denaturing (also referred to as "melting") is the separation of a double stranded polynucleotide (fully or partially duplex) into at least two single strands of polynucleotide by raising the temperature of the solution holding that polynucleotide.

"Hybridization" describes the formation of double stranded or duplex nucleic acid from complementary single stranded nucleic acids. Hybridization may take place between sufficiently complementary single stranded DNA and/or RNA to form: DNA-DNA, DNA-RNA, or RNA-RNA.

"Annealing" refers to hybridization between complementary single chain nucleic acids when the temperature of a solution comprising the single chain nucleic acids is lowered below the melting or denaturing temperature.

The in vitro amplification of DNA is catalyzed by DNA polymerase. A number of types of DNA polymerase are known to the art. They generally share the common property of catalyzing the synthesis of a double stranded DNA sequence utilizing a single stranded template to which a primer is annealed. DNA polymerases extracted from most organisms become inactive at the temperatures required for thermal denaturing of nucleic acids. Thus, replacement of the enzyme at the start of each thermal cycle, or the addition of a factor able to prevent heat inactivation, is required if such heat sensitive enzymes are utilized. The DNA polymerases which are preferred for in vitro PCR as well as for the invention are derived from organisms which thrive at high temperatures and thus are heat resistant (do not lose catalytic activity at the temperature which denatures duplex DNA).

The reaction catalyzed by DNA polymerase is known to the art, and referred to herein as the "DNA polymerase reaction". The reaction as modified herein requires a buffer solution as known to the art, a supply of DNA template (the DNA sequence of interest), some or all (depending on template sequence composition) of the four deoxyribonucleotide triphosphates (which may include modified bases as described above), a single specific primer designed to hybridize to or near the 3' terminal of the template, preferably used in a molar excess of 1000:1 with respect to the nucleic acid of interest, and a means for cyclic strand separation. Strand separation is preferably achieved by thermal cycling between annealing and denaturation temperatures. Reverse transcriptase is known to mediate both RNA to DNA copying, as well as DNA to DNA copying. Hence, any number of enzymes now known will catalyze the chain reaction.

"Electrochemiluminescent (ECL) labels" are those which become luminescent species when acted on electrochemically. A chemical moiety with such properties is one having the formula

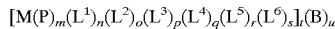

wherein M is ruthenium, rhenium or osmium; P is a polydentate ligand of M; $L^1$, $L^2$, $L^3$, $L^4$, $L^5$, and $L^6$ are ligands of M, each of which may be the same as, or different from, each other ligand; B is a substance covalently bound to one or more of P, $L^1$, $L^2$, $L^3$, $L^4$, $L^5$, and $L^6$ through one or more amide or amine linkages; m is an integer equal to or greater than 1; each of n, o, p, q, r and s is zero or an integer; t is an integer equal to or greater than 1; u is an integer equal to or greater than 1; and P, $L^1$, $L^2$, $L^3$, $L^4$, $L^5$, and $L^6$ and B are of such composition and number that the chemical moiety can be induced to emit luminescence and the total number of bonds to M provided by the ligands of M equals the coordination number of M. Electrochemiluminescent techniques are an improvement on chemiluminescent techniques. They provide a sensitive and precise measurement of the presence and concentration of an analyte of interest.

For example, one electrochemiluminescent method detects, in a predetermined volume of a multicomponent, liquid sample an analyte of interest present in the sample at a concentration below about $10^{-3}$ molar, and comprises: a) contacting a sample with a reagent (i) capable of being induced to repeatedly emit electromagnetic radiation upon exposure to an amount of electrochemical energy from a suitable source effective to induce the reagent to repeatedly emit radiation and (ii) capable of combining with the analyte of interest, the contact being effected under appropriate conditions such that the analyte and the reagent combine; b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation and c) detecting electromagnetic radiation so emitted and thereby detecting the presence of the analyte of interest in the sample.

In such techniques, the sample is exposed to a voltammetric working electrode in order to trigger luminescence. The light produced by the label is measured and indicates the presence or quantity of the analyte. Such ECL techniques are described below and are further disclosed in PCT published applications by Bard et al. (11) and Massey et al. (12,13, 23,24).

An "ECL assay buffer" is a general diluent which contains tripropylamine that is necessary for the electrochemical reaction on the electrode in an ECL analyzer.

An "ECL diluent" is a diluent reagent used in diluting solutions containing labile biomolecules for storage purposes.

The terms "detection" and "quantitation" are referred to as "measurement", it being understood that quantitation may require preparation of reference compositions and calibrations.

"ECL apparatus" is any apparatus for performing electrochemiluminescence based assays.

Tag NHS (N-hydroxy-succinimide) and tag phosphoramidite are examples of ECL tags. The tag-NHS ester is useful for labeling substances containing free amino groups capable of reaction with the NHS ester to form an amide bond. (See, for example, WO86/02734). The tag phosphoramidite is useful for labeling substances containing free amino, sulphydryl, or hydroxyl groups forming phospholinkages, especially phosphodiester linkages.

Selection of Primer for Single Primer Amplification.

Any oligonucleotide complementary to the approximately 10–40 bp sequence of the 3' terminal of the nucleic acid sequence of interest may be chosen as the first putative primer for practicing single primer amplification.

It has been discovered that the majority of primers so selected provide successful amplification after manipulation of the various polymerase reaction parameters well known to the art.

While not wishing to be held to any particular hypothesis as to the mechanism of action of single primer exponential amplification, it is believed that transition from linear amplification to exponential amplification occurs upon insertion of a primer site into the copy of the nucleic acid sequence of interest in a region 5' to the original or first primer site. Thus, exponential amplification proceeds because there are two templates each having a primer site. The single primer amplifies both templates and exponential amplification follows. In any nucleic acid sequence of interest the likelihood is great that a second primer site will be inserted at another location on the nucleic acid 5' from the original primer site during the linear amplification steps. Most primers selected as fully complementary with the approximately 3' terminal of the nucleic acid sequence of interest have provided exponential amplification after a number, i.e., 30–60, of cycles of the polymerase reaction.

For those first putative primers which do not provide single primer exponential amplification, a second, or third or $n^{th}$ putative primer may be used, or, a more detailed, but still routine, effort may be made to create a modified putative primer. As described above, it is well known to the art that even paired primer amplification may require some routine effort to overcome difficulties in the practice of the amplification process.

It has now been determined that the putative single primer may be designed to hybridize to the 3' terminal of the nucleic acid sequence of interest, and may be at least complementary to a second region of the nucleic acid sequence of interest. The degree of complementarity of the first putative primer to the second primer site on the nucleic acid sequence may be as low as 7.5%–30%, or as high as 100%, however, it is not required that the putative primer hybridize with the second primer site.

A generalized procedure for single primer selection is as follows: a sequence of about 10–40 bases located at or near the 3' terminal of a nucleic acid sequence of interest is selected as the first priming site, and a complementary oligonucleotide is prepared. The complementary oligonucleotide is the first putative primer. Primers selected by this procedure have generally been effective to provide successful single strand priming without more selection.

The sequence of a first putative single primer may be compared to the region of the selected nucleic acid sequence of interest 5' from the first primer site, in order to identify additional complementary sequences between the first putative primer and the selected nucleic acid sequence. The complementary sequences should be within 5 kb of the first priming site and preferably, within 2 kb of the first priming site. If one or more sequences within the nucleic acid sequence of interest are found to be at least 7.5% and preferably 30% complementary to the first putative primer, then it can be expected that single primer exponential amplification will be achieved. Confirmation is obtained by carrying out the method of the invention.

If this strategy does not result in successful priming, a second, or third, or $n^{th}$ putative primer may be obtained by shifting the first priming site one base at a time towards the 5' terminal of the nucleic acid sequence of interest. The sequence of each successive putative primer may be compared with sequences within the nucleic acid sequence of interest to determine the likelihood of success of such primer as described above. Ultimate confirmation is achieved by carrying out the method of the invention.

If shifting the first priming site fails to result in a primer providing successful single primer exponential amplification, then the sequence data generated during this process may be used to design a primer having the greatest complementarity with a potential second priming site on the nucleic acid sequence of interest and, preferably complementary with the 3' region thereof. These modified primers may be varied one base at a time, to create a series of optimized modified putative primers of increasing complementarity with the potential second priming site, but of decreasing complementarity with the first priming site. The resulting series of putative primers may then be screened to identify a successful primer.

In order to better understand the invention a number of examples illustrating some of the various ways in which single primer amplification may be carried out are provided. The examples are not intended to in any way limit the scope of the invention, but are provided to illustrate the invention to the skilled artisan.

EXAMPLE I

Synthesis of Label (Tag-Phosphoramidite)

1(a). Synthesis of THP-Derivative of Bromo Alkanol

This synthetic scheme may be better understood by referring to Scheme 1a) below.

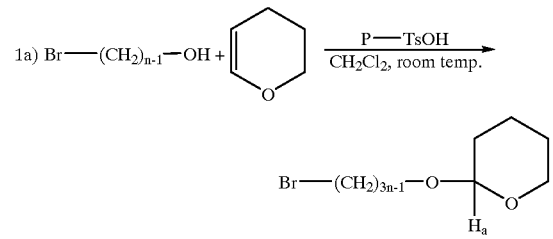

The following procedure is for the synthesis of bipyridine ligand with 4-carbon spacer arm. However, the same synthesis procedure has been used without any modification for the synthesis of a 7-carbon bipyridine ligand using THP-derivative of bromohexanol.

3-bromo-1-propanol, 12.5 g (~90 mmole), was placed in a 250 ml round bottom flask. Dichloromethane, 50.0 ml, and 100 mg P-toluenesulfonic acid were added to the flask. The solution was stirred on a magnetic stir plate. 3,4-dihydro-2H-pyran, 9.2 g (~110 mmole), was dissolved in 80 ml of dichloromethane and the resulting solution was placed in a pressure equalized addition funnel. The 3,4-dihydro-2H-pyran solution in the addition funnel was added to the solution in the flask over a period of 1 h. The solution in the flask turned either a light or dark green in color. The progress of the reaction was checked by TLC on silica-gel plate in 50% hexane: 50% ethylacetate. The TLC plate was developed by dipping the plate in a solution of phosphomolybdic acid and warming it on a hot plate. The product, a THP-derivative of 3-bromo-1-propanol has an $R_f$_1.0, and the unreacted 3,4-dihydro-2H-pyran has an $R_f$_0.5 (exhibits streaking). The TLC demonstrated that the reaction went to completion in about 1 hour after the addition of the 3,4-dihydro-2H-pyran as indicated by a major single spot with an $R_f$_1.0. The reaction was then quenched by the addition of 100 ml of 20% sodium bicarbonate solution followed by extraction of the aqueous layer twice with 100 ml of dichloromethane. The combined dichloromethane layer was dried over 50 g anhydrous sodium sulfate and rotary evaporated to obtain an oily product.

The final (oily) product was purified by silica gel column chromatography using 5% ethyl acetate: 95% hexane as the mobile phase. The chromatography was monitored by TLC using the solvent conditions described above. Fractions containing pure product were pooled and the solvent was removed by rotary evaporation, resulting in 16.0 g of pure, clear oily product. The yield of this reaction step was about 75±5%.

The $^1$H-nmr spectrum shows a multiplet at 4.55 ppm which is characteristic of the $H_\alpha$ proton of the THP-group (as shown in reaction scheme I).

$^1$H-nmr spectral data of THP-derivative of 3-bromo propanol: $^1$H-nmr (CDCl$_3$), δ 1.30–1.80(m,6); 2.06(qn., 2); 3.40–3.50(m,4); 3.74–3.83(m,2) and 4.50–4.57(m,1).

1(b). Alkylation Reaction

This synthetic scheme may be better understood by referring to Scheme 1b) below.

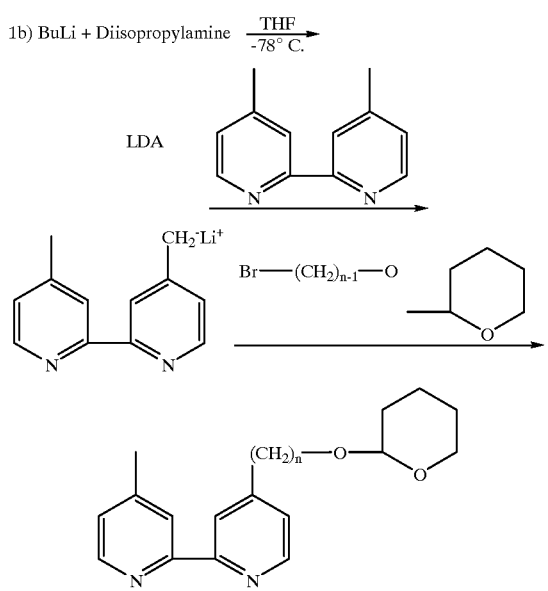

The procedure utilized the in situ generation of lithium diisopropylamide (LDA). A 500 ml round bottom flask was dried in an oven and cooled in a desiccator in order to remove moisture prior to use. Diisopropylamine, 3.1 ml (_22 mmole), was placed in the 500 ml round bottom flask together with 15.0 ml of dry tetrahydrofuran (THF). The mouth of the flask was equipped with a three-way stopcock. One of the outlets of the stopcock was connected to an argon-filled balloon and the other outlet was sealed with a rubber septum in order to facilitate introduction of reagents using a syringe. The flask was cooled at −78° C. in a constantly stirred dry ice—isopropyl alcohol cooling bath to which both dry ice and isopropyl alcohol were added as needed to maintain the bath temperature. After half an hour 14.0 ml (_22 mmole) of butyllithium was slowly added to the diisopropylamine solution. After the addition, the reaction flask was carefully raised from the cooling bath for 10 min., and then re-immersed into the cooling bath.

4,4'-dimethyl-2,2'-bipyridine, 3.68 g (_20.0 mmole), was ground into a fine powder in a pestle and mortar. This was dissolved in 80.0 ml of dry tetrahydrofuran (THF) in a 250 ml round bottom flask. The reaction flask was raised just above the surface of the cooling bath, and the bipyridine solution was slowly added. Upon addition of the bipyridine solution the reaction mixture turned dark purple in color. After the complete addition of the bipyridine solution, the flask was re-immersed in the cooling bath and the reaction mixture was stirred in the cooling bath for two hours. A THP-derivative of 3-bromo-1-propanol, 6.0 g (_26.0 mmole), was placed in a 100 ml round bottom flask and then about 10–15 ml dry THF was added and the solvent was evaporated on a rotary evaporator. The process of addition and evaporation of dry THF was repeated two more times, and each time the vacuum was released to argon. Finally, the residue was dissolved in 5.0 ml of dry THF and the resulting solution was added to the reaction mixture and stirred for another hour. The reaction was checked by TLC on silica-gel plate with 10% methanol: 90% chloroform as the mobile phase. The TLC revealed two spots.

The slower moving (unreacted) 4,4'-dimethyl-2,2'-bipyridine has an $R_f$_0.35, and the faster moving alkylated product has an $R_f$_0.42. A successful reaction was indicated when the TLC spot corresponding to the desired product represented more than 60% by mass with respect to untreated starting material. The reaction mixture was then allowed to stir overnight. No further addition of either the dry ice or the isopropyl alcohol to the cooling bath was necessary.

The TLC of the reaction was checked again the next day. The reaction was then quenched by adding 100 ml of saturated NH$_4$Cl solution and the quenched mixture was transferred to a separatory funnel. After shaking, followed by settling of the mixture, the solution separated into a bottom aqueous layer and a top THF layer. The THF layer was then separated and dried over anhydrous sodium sulfate. The aqueous layer was extracted twice with 150 ml of dichloromethane. The combined organic layer was dried over anhydrous sodium sulfate and rotary evaporated to obtain an oily residue. The reaction mixture was purified after the deprotection of THP group as described below in 1(c).

1(c). Deprotection of THP-Group and Purification by Column Chromatography

This synthetic scheme may be better understood by referring to Scheme 1c) below.

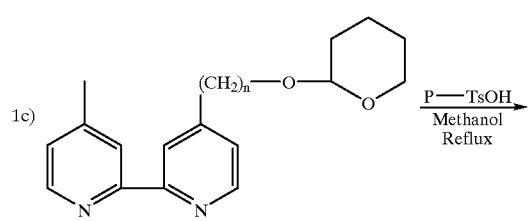

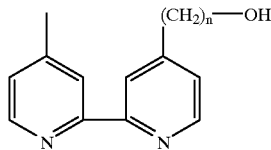

The $R_f$ difference between the unreacted 4,4'-dimethyl-2,2'-bipyridine and the alkylated product is very small. Hence, it is preferable to carry-out the purification of the bipyridine ligand after the deprotection of the THP-group which results in a considerable $R_f$ difference between the desired product and the impurity.

| COMPOUND | $R_f$ |
| --- | --- |
| THP-derivative of 4-carbon bipyridine ligand | 0.42. |
| 4,4'-dimethyl-2,2'-bipyridine (unreacted) | 0.35. |
| 4-carbon bipyridine ligand (alcohol ligand) | 0.15. |

40 ml of methanol was added to the oily residue from the alkylation reaction (section 1(b)) and placed in a 250 ml round bottom flask. The oily residue contains a mixture of unreacted 4,4'-dimethyl-2,2'-bipyridine, THP-derivative of bipyridine ligand (the desired product), and the unreacted THP-derivative of 3-bromo-1-propanol. P-toluenesulfonic acid, 5.0 g (_25 mmole), was added to the reaction mixture followed by stirring at room temperature for 1 h. The reaction was monitored by TLC on silica gel plates with 10% methanol: chloroform as the mobile phase. The $R_f$ values for various components were: unreacted 4,4'-dimethyl-2,2'-bipyridine $R_f$_0.35, THP-derivative of bipyridine ligand with spacer arm $R_f$_0.42, and the bipyridine alcohol ligand with the spacer arm $R_f$_0.15. Completion of the reaction was indicated by the disappearance of the spot corresponding to the THP-derivative of bipyridine ligand ($R_f$_0.42) on TLC. The solvent (methanol) was then evaporated on a rotary evaporator, and the residue resuspended in 10 ml of dichloromethane, to which 40.0 ml of saturated solution of sodium bicarbonate was added. The aqueous layer was then extracted twice with 100 ml of dichloromethane. The combined organic layer was dried over anhydrous sodium sulfate, and the solvent was stripped-off on a rotary evaporator, yielding an oily residue as the product.

The oily product was purified by silica gel column chromatography using 2% methanol: 98% chloroform as mobile phase. The column was monitored by TLC on silica gel with 10% methanol: 90% chloroform. The pure fractions (as judged by TLC) were pooled and the solvent was removed by rotary evaporation. The yield of the alkylation reaction was very much dependent on the maintenance of dry conditions during the reaction as well as on the freshness of reagents such as butyllithium. The yield of this alkylation reaction step was about 60±10%. The compound was characterized by recording a $^1$H-NMR spectrum of the sample.

$^1$H-NMR spectral data of bipyridine alcohol ligand: $^1$H-NMR (CDCl$_3$), δ 1.54–1.64(m,2); 1.68–1.80(m,2); 2.45 (s,AR-cH$_3$); 2.66–2.75(t,2); 3.59–3.68(t,2); 7.09–7.20(m,2 Ar-H); 8.20 (S,2 Ar-H) 8.50–8.60(m,2 Ar-H)

2. Preparation of Tris-Bipyridine Ruthenium (II) Complex Tag-Alcohol)

This synthetic scheme may be better understood by referring to Scheme 2) below.

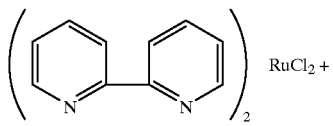

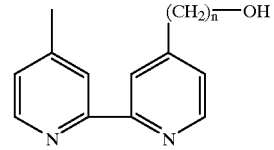

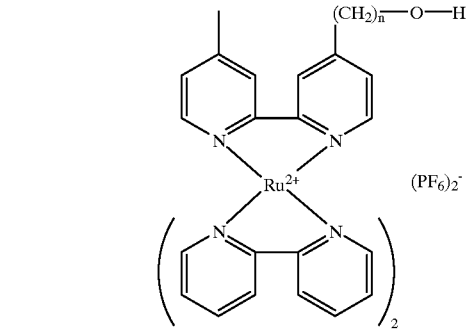

Cis-dichloro-bis(bipyridine) ruthenium (II) dihydrate, 1.040 g (2.0 mmole), and 530.0 mg (_2.2 mmole) of 4-carbon bipyridine ligand (from section 1C), were placed in a 250 ml round bottom flask, 50.0 ml of 10% ethanol in water was added, and the solution was purged with argon gas for 10–15 min. The flask was fitted with a water cooled condenser, and the mixture was refluxed for 6 h to form the tris-bipyridine ruthenium (II) complex. The flask was covered with aluminum foil during refluxing. The solvent was removed by rotary evaporation, and the complex was then dissolved in a minimum amount of deionized water and loaded onto the ion-exchange column.

The usual purification procedure used 7.0 g of the ion-exchange resin to purify 1.3 g (_2.0 mmole) of the complex by column chromatography. The resin was allowed to swell in 300 ml of deionized water for 2–3 h, and then the swelled resin was packed into a column 30 cm in length and 2.5 cm in inner diameter to a height of 15 cm. The resin was then layered with washed and dried sand to a height of 0.5 cm and the column washed with 250 ml of deionized water. The Tag- alcohol from the complex formation reaction from section 2 was dissolved in a minimum amount of deionized water and was carefully layered onto the top of the resin. The chromatogram was developed by washing the column with 250 ml of deionized water. During this wash step, a light yellow colored impurity began separating from the main band (deep-red in color). This impurity was driven-off the column by washing the column with _350 ml of 10 mM NaCl solution. The eluant was later switched to 100 mM NaCl solution. After this, the main deep-red colored band began eluting, and most of the desired product was eluted in a volume of 500–600 ml. A dark brown colored material was adsorbed onto the column permanently and was not eluted from the column even under very high ionic strength buffer (2–3 M HCl and NaCl).

The eluted Tag-alcohol was then precipitated using ammonium hexafluoro-phosphate by the following procedure. The eluate was heated to boiling with constant stirring, and then allowed to cool to 75–80° C., followed by the addition of ammonium hexa-fluorophosphate in small amounts, using a spatula, until a stable precipitate appeared (precipitate appeared and did not go into solution again).

The solution was first brought to room temperature (20–25° C.) and then cooled to 4° C. overnight. The resulting precipitate was collected on a Buchner funnel fitted with a fritted disc (10–15 μ), and then dried under vacuum. The average yield of this complexation reaction after column purification was found to be >80%. The molecular weight of the complex at this stage is ~945.45 (excluding water of hydration).

The Tag-alcohol prepared and purified by the above procedure was then analyzed by HPLC and $^1$H-nmr spectroscopy. HPLC characterization was performed on Perkin-Elmer HPLC instrument with a Beckman $C_{18}$-reverse phase column. The mobile phase consisted of buffers: A) 50 0.10 M triethylammonium acetate, pH 7.25: 50% acetonitrile, and B) 90% acetonitrile: 10% 0.10 M triethylammonium acetate, pH 7.25. The chromatography was run under isocratic condition with 80% buffer B. The flow rate was maintained at 1.0 ml/min., and elution was monitored by absorbance at 280 nm.

Tag-alcohol, 2.0 mg, was dissolved in 100 μl of buffer B. Then 1.0 μl of this stock solution was diluted to 400 μl with buffer B. 50 μl of this diluted solution was injected into the HPLC instrument. The tag-alcohol eluted as a single major peak between 22–23 min. The purity of the Tag-alcohol, as determined by integration of the elution peak, was 95±3%.

The $^1$H-nmr spectrum was recorded on a GE-300 MHz FT-nmr instrument. In a typical analysis, 30 mg of Tag-alcohol was dissolved in 500 μl of $CD_3CN$. The $^1$H-NMR also clearly indicated that the purity of the material was satisfactory.

$^1$H-NMR spectral data of Tag-alcohol: $^1$H-NMR ($CD_3CN$) δ 1.52–1.65(m,2); 1.72–1,85(m,2); 2.20(s,3 Ar—$CH_3$); 2.82–2.90(m,2); 3.50–3.60(m,2); 7.23–7.32(m, 2, 5' Ar—H); 7,38–7.48(m,4, 4 Ar—H); 7.42–7.52(m,2 3' Ar—H); 7.52–760(m,4, 3 Ar—H); 8.02–8.14(m,4, 5 Ar—H); 8.38–8.44(d,2, 6' Ar—H) and 8.50–8.56(d,4, 6 Ar—H).

3. Phosphitylation Reaction

This synthetic scheme may be better understood by referring to Scheme 3) below.

flask. 10 ml of freshly distilled dry acetonitrile (distilled over $CaH_2$) was added and rotary evaporated. The addition and evaporation of dry acetonitrile was performed three times to ensure that the material was devoid of moisture. Finally, the mixture of tag-alcohol and tetrazole was redissolved in 3.0 ml of dry acetonitrile. During the course of the entire sequence of operations the reaction flask was maintained under argon atmosphere. 2-cyanoethyl-N,N,N',N'-tetra-isopropylphosphorodiamidite (phosphitylating agent), 500 μl (~1.6 mmole), was added to the stirring reaction mixture. The reaction was allowed to proceed for 1 h., covered by aluminum foil. The reaction was stopped by addition of 10.0 ml of a saturated sodium chloride solution and the aqueous layer was extracted thrice with 25 ml of dichloromethane. The combined organic layer was dried over anhydrous sodium sulfate and the solvent was removed by rotary evaporation. The foamy residue was dried extensively under vacuum. The material was dissolved in 15–20 ml of dry dichloromethane and the solution was slowly added to a stirring solution of dry pentane. It is preferable to carry-out this precipitation step in a glove box under an argon atmosphere. After the addition of about 10 ml of the tag-phosphoramidite solution, the precipitate was allowed to settle-down. The pentane (supernatant) was carefully decanted-off and was replenished with fresh pentane followed by addition of remaining tag-phosphoramidite solution. After the complete addition of the tag-phosphoramidite solution, the precipitate was stirred in pentane solution for half an hour more. The supernatant was decanted carefully, and the traces of solvent were removed under vacuum. The final product was an amorphous powder, and it was extensively dried under vacuum. The product was characterized by $^{31}$P-nmr spectroscopy. The yield of the phosphitylation reaction after the precipitation step has been consistently found to be >75%.

The tag-phosphoramidite was characterized by $^{31}$P-nmr. The sample was prepared by dissolving 45.0 mg of tag-phosphoramidite in 500 μl of $CD_3CN$. The spectrum was recorded on a JEOL 270 MHz Ft-nmr instrument with 85% phosphoric acid as the external standard.

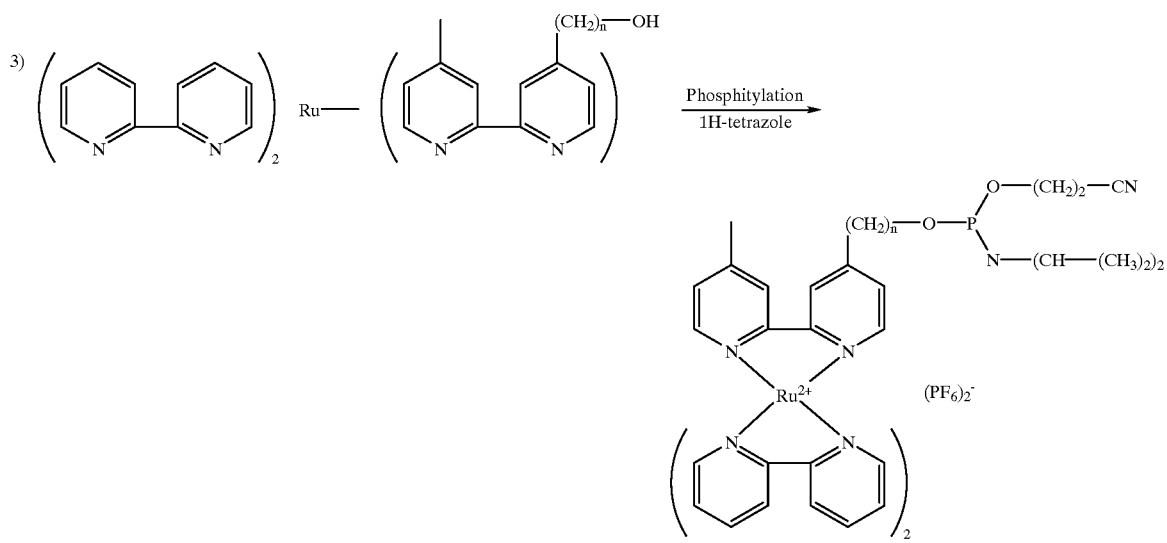

Tag-alcohol, 945 mg (~1 mmole), and 35.0 mg (~0.5 mmole) of lH-tetrazole were placed in a 50 ml round bottom $^1$H-NMR spectral data of tag-phosphoramidite: $^1$H-NMR ($CD_3CN$), δ 1.10–1.21(m,12); 1.61–1.72(m,2); 1.76–1.85

(m,2); 2.1(s,3 Ar—CH₃); 2.62–2.68(t,2); 2.82–2.88(t,2); 3.52–3.83(m,6); 7.25–7.30(m,2, 5' Ar—H); 7.39–7.46(m,4, 4 Ar—H), 7.55–7.61(m,2, 3' Ar—H); 7.75–7.80(m,4, 3 Ar—H); 8.03–8.12(m,4, 5 Ar—H); 8.39–8.45(d,2, 6' Ar—H) and 8.51–8.56*d,4, 6 Ar—H).

EXAMPLE II

Oligonucleotide Synthesis

The oligonucleotides were made on an Applied Biosystems (San Jose, Calif.) automated oligonucleotide synthesizer using the β-cyanoethyl phosphoramidite chemistry (17). Oligonucleotide amino modifications to the 5' end occurred at the last coupling step. Clontech (San Diego, Calif.) supplied the amino modifiers. The resulting 5' modified oligonucleotides all contain a six carbon spacer arm to the amino group, designated (C6, NH2). Some of the sequences were labeled directly during synthesis using the tag-phosphoramidite. Oligonucleotide Ru(II) modifications to the 5' end occurred at the last coupling step using the tag-phosphoramidite (0.4 M) on the Applied Biosystems automated oligonucleotide synthesizer, designated as Ru(II), in the following oligonucleotide. The oligonucleotides which were constructed, their modifications and utility are described below.

A. Oligonucleotides INFG2 (SEQ ID NO:1) and INFG3 (SEQ ID NO:2) for amplification of the human interferon gamma gene (18).

INFG2 (C6, NH2) CTCCACACTCTTTTGGATGCTCTG-GTCATC;

INFG3 (C6, NH2) CACATCATCCTCTGTTTGT-GCTCTTTCCT.

B. oligonucleotides for human papilloma virus (HPV) directed to the E6 region (19), oligonucleotide sequences 2PV16 (SEQ ID No:3), 3PV16 (SEQ ID NO:4), 3PV16p (SEQ ID NO:4), 2PV18 (SEO ID NO:5), 3PV18 (SEO ID No:6).

For HPV16:

2PV16 5' (C6, NH2) CAGTTAATACACCTAATTAA-CAAATCACAC;

3PV16 5' (C6, NH2) ACAACATTAGAACAGCAATA-CAACAAACCG; and

3PV16p 5' Ru(II):ACAACATTAGAACAGCAATACAA-CAAACCG.

For HPV18:

2PV18 5' (C6, NH2) CACCGCAGGCACCTTAT-TAATAAATTGTAT;

3PV18 5' (C6, NH2) GACACATTGGAAAAACTAAC-TAACACTGGG.

These oligonucleotides enable the amplification of the fragments 3PV16 or 3PV18 for HPV 16 and 18 DNA respectively, with biotinylated 2PV16 or 2PV18 for capture of the respective amplified products.

C. Oligonucleotides TRP.C03 (SEQ ID NO:7) and TRP.C04 (SEQ ID NO:8) specific for the Trp E/D region of the *Escherichia coli* genome (20, 21).

TRP.C03 5' (C6,NH2) GCCACGCAAGCGGGTGAGGAGTTCC(NH2) was labeled with biotin and

TRP.CO4 5' (C6,NH2) GTCCGAGGCAAATGC-CAATAATGG was labeled with tag-NHS ester label as described below.

EXAMPLE III

Labeling Oligonucleotides

All the synthetic oligonucleotides were purified to remove any contaminating amino groups by gel filtration on a BIOGEL™ P6 (Bio-Rad Labs, Richmond, Calif.) column. Biotin was introduced via the 5'-amino group of the oligonucleotides using NHS-biotin (Clontech, San Diego, Calif.). Tag-NHS ester label (an NHS ester of the Ru tris bipyridyl complex) was introduced via the amino group of the modified oligonucleotides as follows. The oligonucleotides (0.1 μmole) in 100 μl of PBS (pH 7.4) were reacted with 0.5 μmole of tag-NHS ester label dissolved in DMSO overnight at room temperature in the dark. Oligonucleotides were recovered from these labeling reactions by ethanol precipitation.

EXAMPLE IV

Preparation of Streptavidin Magnetic Beads

To 15 mg of BSA (in 2–3 ml PBS), 105 μl of dimethylsulfoxide containing 50 mg/ml of biotin-x-NHS (Clontech, San Diego, Calif.) was added followed by mixing and incubation at room temperature for 30 minutes. The reaction was stopped by adding 30 μl of 1M glycine and incubation at room temperature for 10 minutes. The reaction mix was purified by gel filtration chromatography (Bio-Gel P6, Bio-rad Labs, Richmond, Calif.). This biotin-BSA was filtered using a 0.2 μm filter and syringe. 5 mg biotin-BSA in 10 ml of 0.2 M sodium carbonate/bicarbonate buffer pH 9.6 was added to 300 mg of DYNABEADS™ (DYNAL #14002) (DYNABEADS is a trademark of DYNAL, Great Neck, N.Y.) (the beads comprise either:

(i) Dynal M-450 Dynabeads, 4.5 μm diameter superparamagnetic particles, 30 mg/mL, obtained from Dynal, 45 North Station Plaza, Great Neck, N.Y. 11021; or (ii) Dynal M-280 Dynabeads, 2.8 μM diameter superparamagnetic particles, 10 mg/mL, obtained from Dynal, 45 North Station Plaza, Great Neck, N.Y. 11021)

washed with carbonate/bicarbonate. This mixture was vortexed, and incubated overnight at room temperature with mixing. The beads were magnetically separated followed by the addition of 10 ml ECL diluent (37.5 mM $KH_2PO_4$, 109.2 mM $K_2HPO_4.3H_2O$, 151.7 mM NaCl, 0.65 mM $NaN_3$, 0.43 mM bovine serum albumin in $H_2O$) and 100 μl tRNA (10 mg/ml). This mixture was incubated for 3–4 hours at room temperature with mixing. The beads were washed once with 10 ml of ECL diluent and resuspended in 10 ml of ECL diluent and 100 μl tRNA (10 mg/ml). This mixture was mixed and incubated at 2–6° C. overnight to stabilize proteins on beads. The beads were magnetically separated and suspended in 10 ml of phosphate buffered saline (PBS) containing 15 mg of streptavidin (Scripps Laboratories, San Diego, Calif., catalog number S1214) followed by mixing for one hour. The beads were washed 4 times in 10 ml ECL diluent, with 5 minutes mixing for each wash. The beads were finally resuspended in 29.7 ml of ECL diluent and 300 μl tRNA (10 mg/ml) to a final concentration of 10 mg/ml particles +100 μg/ml tRNA.

EXAMPLE V

Amplification of Human Interferon Gamma Gene

A. Amplification procedure.

The amplification reaction was set up as follows. A reaction mixture was prepared containing dATP 200 μM, dCTP 200 μM, dGTP 200 μM, dTTP 200 μM, $MgCl_2$ 2 mM, Tris-HCL 10 mM, pH 8.3, 50 mM KCl, Primer 0.5 μM, AmpliTaq™ (Perkin Elmer-Cetus, Norwalk, Conn.) 40 Units/ml and sample DNA 1 μg. The primer used was the INFG3 primer (Ex. IIA) labeled with tag-NHS ester. The DNA samples were human placental DNA (Sigma, St.

Louis, Mo.) and Salmon sperm (SS) DNA (Sigma) as the control. This reaction mix was subjected to 80 cycles of 97° C. for 10 sec and 50° C. for 1 sec in a Perkin Elmer-Cetus DNA thermal cycler. The samples were analyzed for amplification by hybridization with 2 ng of INFG2 (SEQ ID NO:1) labeled with biotin to 90 µl of sample for 30 min at 55° C. These hybridized samples were then incubated with 20 kg of streptavidin beads for 30 min at room temperature with shaking to capture the biotinylated probe. These beads were then washed three times with ECL assay buffer (112 mM $KH_2PO_4$, 88 mM $K_2HPO_4.3H_2O$, 50 M NaCl, 6.5 mM $NaN_3$, 0.8 µM Triton X-100, 0.4 mM Tween 20, 100 mM tripropylamine) and the samples of beads resuspended in ECL assay buffer and read on an ECL analyzer to determine the level of electrochemiluminescence (ECL) expressed as numbers of ECL counts. The result was as follows: for the salmon sperm DNA, 62 counts; and for the human placental DNA, 22961 counts. This result demonstrated the specific amplification of the interferon gene segment of interest.

B. Evaluation of Amplification by Southern Blot.

In order to evaluate the nature of this amplification, a Southern blot analysis was performed upon amplified product. Ten µl of the INFG3 amplified human DNA sample (equivalent to 100 ng of starting DNA), 10 µl of INFG3 amplified salmon sperm DNA, 1 µg of human placental DNA and DNA size markers were subjected to gel electrophoresis followed by transfer to nitrocellulose membrane (22). This blotted DNA was then subjected to hybridization with the INFG2 (SEQ ID NO:1) biotinylated probe followed by detection using a streptavidin alkaline phosphatase kit following recommended procedures (Life Technologies, Gaithersburg, Md.). The result of this test was the demonstration of two strongly hybridizing species in the amplified sample. These species were estimated based on the DNA size markers to be of 620 and 590 base pairs. As expected the unamplified human DNA did not show any signal nor did the salmon sperm amplified controls. This data from the Southern blot analysis supports the conclusion from the ECL assay that single primer amplification was observed.

EXAMPLE VI

Amplification of Human Papilloma Virus 16 (HPV16) DNA

A. Amplification procedure.

The amplification reaction was set up as follows. A reaction mixture was prepared containing dATP 200 µM, dCTP 200 µM, dGTP 200 µM, dTTP 200 µM, $MgCl_2$ 2mM, Tris-HCL 10 mM, pH 8.3, 50 mM KCl, Primer 0.5 µM, AmpliTaq® (Perkin Elmer-Cetus) 40 Units/ml and sample DNA 1 µg. The primer used was the 3PV16 (SEQ ID NO:4) primer labeled with tag-NHS ester. The DNA samples were HPV16 DNA (24) and Salmon sperm DNA (Sigma) as the control. This reaction mixture was subjected to 80 cycles of 97° C. for 10 sec and 50° C. for 1 sec in a Perkin Elmer-Cetus DNA thermal cycler.

The samples were analyzed for amplification by hybridization with 2 ng of 2PV16 labeled with biotin to 90 µl of sample for 30 min at 55° C. These hybridized samples were then incubated with 20 µg of streptavidin beads for 30 min at room temperature with shaking to capture the biotinylated probe. These beads were then washed three times with ECL assay buffer and the samples of beads resuspended in ECL assay buffer and read on an ECL analyzer to determine the level of ECL. The result was as follows expressed in ECL counts. For the salmon sperm DNA, 67 counts, and for the HPV16 DNA, 32444 counts. This result demonstrated the specific amplification of the HPV16 DNA of interest.

B. Evaluation of Amplification by Southern Blot.

In order to evaluate the nature of this amplification a Southern blot analysis was performed. Ten Al of the 3PV16 amplified HPV16 DNA sample (equivalent to bong of starting DNA), 10 µl of 3PV16 amplified salmon sperm DNA, 1 µg of HPV16 DNA and DNA size markers were subjected to gel electrophoresis followed by transfer to nitrocellulose membrane (24). This blotted DNA was then subjected to hybridization with the 2PV16 biotinylated probe followed by detection using streptavidin alkaline phosphatase kit following recommended procedures (Life Technologies, Gaithersburg, Md.). The result of this test was the demonstration of a strongly hybridizing species in the amplified HPV16 DNA sample. This species was estimated, based on the DNA size markers, to be 870 base pairs. The unamplified HPV16 DNA did not show any signal nor the salmon sperm amplified controls. This data from the southern blot analysis supports the conclusion based on ECL assay evidence that single primer amplification was achieved.

EXAMPLE VII

Amplification of *Escherichia coli* DNA

The amplification reaction was set up as follows. A reaction mixture was prepared containing dATP 200 µM, dCTP 200 µM, dGTP 200 µM, dTTP 200 µM, $MgCl_2$ 2mM, Tris-HCL 10 mM, pH 8.3, 50 mM KCl, Primer 0.5 µM, AmpliTaq® (Perkin Elmer-Cetus) 40 Units/ml and sample DNA 1 µg. The primer used was the TRP.C04 primer labeled with tag-NHS ester. The DNA samples were *Escherichia coli* DNA (Sigma) and Salmon sperm DNA (Sigma) as the control. This reaction mix was subjected to 80 cycles of 97° C. for 10 sec and 50° C. for 1 sec in a Perkin Elmer-Cetus DNA thermal cycler. The samples were analyzed for amplification by hybridization with 2 ng of TRP.C01 labeled with biotin to 90 µl of sample for 30 min at 55° C. These hybridized samples were then incubated with 20 µg of streptavidin beads for 30 min at room temperature with shaking to capture the biotinylated probe. These beads were then washed three times with ECL assay buffer and the samples of beads resuspended in ECL assay buffer and read on an ECL analyzer to determine the level of ECL. The result expressed in ECL counts was as follows: for the salmon sperm DNA, 185 integrated counts; and for the *E.coli* DNA, 1397 integrated counts. This result demonstrated the specific amplification of the Trp gene DNA of interest.

EXAMPLE VIII

Time Course of Amplification

Samples of human placental HPV 16 (CaSki) and HPV18 (HeLa) DNA were subjected to amplification as described above using INFG3 (SEQ ID NO:2), 3PV16p (SEQ ID NO:4) (ECL labeled using the tag-phosphoramidite) and 3PV18 (SEQ ID NO:6) respectively, but samples were removed at cycle numbers 20, 30, 40, 50, 60, and 80. These samples were then analyzed to determine the level of the amplified product as indicated by ECL counts. INFG3 and 3PV18 were labeled using the tag-NHS ester.

TABLE 1

| ECL Results. | Cycle Number | | | | | |
|---|---|---|---|---|---|---|
| Primer/DNA | 20 | 30 | 40 | 50 | 60 | 80 |
| 3PV16p/HPV16 | 72 | 262 | 5234 | 10879 | 7708 | 6662 |
| SS* | — | — | — | — | — | 84 |
| 3PV18/HPV18 | 370 | 583 | 1756 | 6857 | 6794 | 6073 |
| SS | — | — | — | — | — | 148 |
| INFG3/Human | 85 | 53 | 199 | 2785 | 3533 | 5491 |
| SS | — | — | — | — | — | 86 |

*SS = salmon sperm

These results demonstrated that the amplification was occurring by an unexpected method as the levels of the signal generated showed rapid amplification after cycle 30, demonstrating an exponential amplification.

EXAMPLE IX

Optimal Temperature for Amplification

To study the effect of differing temperature cycles on the amplification, different temperature cycles were evaluated. The lower temperature of the two step cycle was varied. The cycle temperatures were 97° C. to 30° C., 97° C. to 40° C., 97° C. to 50° C., 97° C. to 60° C., and 97° C. to 70° C. These cycles are thus referred to by the lower temperature for clarity. In addition, the Ericomp (Twin Block, Ericomp Inc, San Diego, Calif.) thermocycler was used. The other conditions for amplification were as described for the time course above for human interferon and human papilloma virus DNA.

A. Results with the Perkin Elmer DNA thermal cycler.

TABLE 2

| | | Cycle Lower Temperature | | | | |
|---|---|---|---|---|---|---|
| Primer | DNA | 30° C. | 40° C. | 50° C. | 60° C. | 70° C. |
| 3PV16p | HPV16 | 10103 | 16791 | 10579 | 12266 | 61 |
| | SS | 89 | 113 | 130 | 92 | 65 |
| 3PV18 | HPV18 | 50 | 113 | 5595 | 96 | 62 |
| | SS | 73 | 86 | 134 | 125 | 66 |
| INFG3 | Human | 101 | 1348 | 7119 | 6390 | 52 |
| | SS | 63 | 81 | 220 | 917 | 41 |

B. Results with the Ericomp thermal cycler.

TABLE 3

| | | Cycle Lower Temperature | | | | |
|---|---|---|---|---|---|---|
| Primer | DNA | 30° C. | 40° C. | 50° C. | 60° C. | 70° C. |
| 3PV16p | HPV16 | 16307 | 10491 | 9093 | 16346 | 71 |
| | SS | 66 | 106 | 94 | 103 | 66 |
| 3PV18 | HPV18 | 204 | 699 | 8388 | 4731 | 76 |
| | SS | 50 | 51 | 86 | 70 | 73 |
| INFG3 | Human | 190 | 3436 | 6350 | 6617 | 46 |
| | SS | 70 | 72 | 1265 | 993 | 56 |

These results demonstrate the temperature dependent nature of this amplification reaction and indicate the need for optimization of temperatures to allow amplification with certain templates as each particular template-primer combination has a different temperature optimum. The skilled artisan will understand that temperature optimization is often necessary in developing an amplification procedure.

EXAMPLE X

Amplification Using Differing DNA Polymerase Enzymes

DNA polymerase from differing sources was tested to establish that single primer amplification is not enzyme specific.

Reaction mixtures were prepared consisting of the following compositions.

REPLINASE™ (DuPont, Boston Mass.); 50 mM Tris-HCl, pH 9.0, 20 mM ammonium sulfate, 1.5 mM MgCl$_2$ DATP 200 µM, dCTP 200 µM, dGTP 200 µM, dTTP 200 µM, Primer 0.5 µM, 10 µg/ml sample DNA, 40 Units/ml REPLINASE™.

HOT TUB™ DNA polymerase (Amersham, Arlington Heights, Ill.); 25 mM Tris-HCl, pH 9.5 (25° C.), 50 mM KCl, 10 mM MgCl$_2$, 1 mg/ml bovine serum albumin (BSA), dATP 200 µM, dCTP 200 µM, dGTP 200 µM, dTTP 200 µM, 0.5 µM primer, 10 µg/ml sample DNA, 40 Units/ml HOT TUB™ DNA polymerase: PYROSTASE™ (Molecular Genetic Resources, Tampa, Fla.); dATP 200 µM, dCTP 200 µM, dGTP 200 µM, dTTP 200 µM, 50 mM Tris-HCl, pH 9.0(25° C.), 1.5 mM MgCl2, 20 mM ammonium sulfate, 0.01% gelatin, Primer 0.5 µM, 10 µg/ml sample DNA, 40 Units/ml PYROSTASE™: VENT™ DNA polymerase (New England Biolabs, Beverly, Mass.); dATP 200 µM, dCTP 200 µM, dGTP 200 µM, dTTP 200 µM, 20 mM Tris-HCl, pH 8.8, 2 mM MgSO4, 10 mM ammonium sulfate, 10 mM KCl, 0.1% Triton X-100, 0.1 mg/ml BSA, 0.5 µM primer, 10 µg/ml sample DNA, 40 Units/ml VENT™ DNA polymerase: AMPLITAQ® (Perkin Elmer-Cetus) under the conditions described above.

These polymerases were used to amplify samples of HPV16 (CaSki) DNA using primer 3PV16 (SEQ ID NO:4 labeled using tag-NHS ester), and human placental DNA using primer INFG3 (SEQ ID NO:2 labeled using tag-NHS ester). Samples of 100 µl were cycled in the Perkin Elmer-Cetus Thermal cycler using a cycle of 97° C. 10 sec and 50° C. 1 sec for 80 cycles. The HPV and human interferon gamma amplified products were analyzed as above.

ECL assay of amplification products, are expressed as ECL counts.

TABLE 4

| | DNA polymerase | | | | |
|---|---|---|---|---|---|
| Primer/ DNA | AMPLITAQ | HOT TUB | VENT | PYROSTASE | REPLINASE |
| 3PV16p/ HPV16 | 7449 | 9266 | 209 | 7976 | 6935 |
| INFG3/ Human | 5304 | 5570 | 262 | 5599 | 5581 |

These results demonstrate that most DNA polymerases would work with this amplification system with very little optimization of Mg++ or temperature conditions. The poor activity from the Vent DNA polymerase may be due to non-optimal Mg++ conditions.

EXAMPLE XI

Sensitivity of Amplification

Samples of DNA were diluted and subjected to the single amplification as described above using Taq polymerase. The samples were assayed as described above using the biotinylated primers INFG2 (SEQ ID NO:1), 2PV18 (SEQ ID NO:5) and 2PV16 (SEQ ID NO:3). The results are expressed as ECL counts.

TABLE 5

Tag-labeled primers

| DNA (Amount of DNA,ng) | INFG3 Human | SS | 3PV18 HPV18 | SS | 3PV16p HPV16 | SS |
|---|---|---|---|---|---|---|
| 1000 | 13150 | 112 | 1366 | 332 | 12279 | 114 |
| 500 | 12347 | — | 5157 | — | 11895 | — |
| 250 | 12807 | — | 5319 | — | 11717 | — |
| 25 | 7272 | — | 2441 | — | 11121 | — |
| 1 | 2037 | — | 580 | — | 12038 | — |

These results demonstrate the sensitivity of this method. The human interferon gene was detected in only 1 ng of sample DNA. These results are consistent with the data for the HPV DNA samples (Hela and CaSki of Example VIII). The result from the control sample of 1 μg of salmon sperm DNA demonstrates the specificity of this assay system. This demonstrates the utility of the method for diagnosis and detection of specific genes from small sample sizes. The ability of the phosphoramidite labeled primer to undergo single primer amplification efficiently enables the detection of HPV16 in 1 ng of DNA.

EXAMPLE XII

Optimal Primer Concentration.

Preliminary studies were performed utilizing HOT TUB™, PYROSTASE™ and REPLINASE™ (isolated from *Thermus flavis*) polymerases which provided the best results in the previous examples, to determine optimal primer concentrations. Concentrations of 200 ng per 100 μl reaction (0.2 μM) or lower were ineffective. The optimal concentration was about 500 ng per 100 μl reaction (0.5 μM). Above 0.5 μM little improvement was evident. In particular, the PYROSTASE™ and the REPLINASE™ demonstrated better response in comparison to the other polymerases tested during the initial primer study and hence were characterized further. The results from these studies with the tag-labeled INFG3 (SEQ ID NO:2) primer and INFG2 (SEQ ID NO:1) biotinylated probe are illustrated below in TABLE 6. The results are expressed as ECL counts.

TABLE 6

| Polymerase: DNA sample | PYROSTASE ™ Human | SS | REPLINASE ™ Human | SS |
|---|---|---|---|---|
| Amount of primer per reaction | | | | |
| 2 μg | 10522 | 658 | 6597 | 181 |
| 500 ng | 4490 | 132 | 4509 | 225 |
| 200 ng | 227 | 66 | 172 | 65 |

These results demonstrate a broad optimal concentration range for the primers. The lower concentration of 500 ng per 100 μl appears to be best suited to the ORIGEN™ assay system as the background levels tend to be lower and the use of oligonucleotide is more economical. Other assay systems and cloning methods would be expected to have differing optimal concentrations but would generally be expected to follow these values indicated here. The results of this example assay indicated that PYROSTASE™ provided the best results due to its ability to function well at low and at high primer concentrations.

EXAMPLE XIII

Amplification of Human Papilloma Virus (HPV18) DNA

Oligonucleotide 3PV18 (SEQ ID NO:6) was used to amplify 1 μg of HPV18-containing DNA (Hela) and a control containing salmon sperm DNA, using the protocol described earlier with Taq and with cycling from 97° C. to 60° C. in the Ericomp thermocycler. These amplified samples (10 μl i.e. 10% of the amplified sample) were run on a 1% agarose gel together with 1 μg of unamplified material and molecular weight markers. This material was then Southern blotted using known methods and hybridized with a $^{35}$S labeled 2PV18 probe. This probe (as described in Example IIB) has an amino group and was labeled using Amersham's '$_{35}$S labeling reagent' (Amersham, Arlington Heights, Ill.). In brief, 2.5 μg of oligonucleotide was taken and reacted with 50 μCi of the '$^{35}$S labeling reagent' in 10 μl of 80% DMSO overnight. This labeled probe was precipitated from 70% ethanol and washed. The probe was resuspended in 500 μl of hybridization buffer and used at the concentration of 2.5–10$^6$ counts per 5 ml of hybridization solution. The filters were hybridized at 55° C. in 6× SSC, 0.5% SDS, 10 mM EDTA$^3$ then washed in 0.16× SSC, 0.1% SDS at 60° C. and dried. The filters were next sprayed with ENHANCE™ (NEN, Boston, Mass.) and placed under film. The result of this hybridization experiment was the detection of specific products from the single primer amplification of the HPV18 containing DNA. The estimated size of the major product was determined to be about 2000 bases, with the molecular weight standards used. The other samples did not demonstrate any hybridization even though 10 fold more material was loaded of the unamplified material. This demonstrated the ability of the single primer amplification to amplify a single species.

REFERENCES

1. Mullis, K. B. and Faloona, F. A., "Specific Synthesis of DNA In vitro via a Polymerase-Catalyzed Chain Reaction", *Methods in Enzymology* 155: 335–350 (1987).
2. Mullis, K. B., U.S. Pat. Nos. 4,683,195 and 4,683,202.
3. Kim H. -S. and Smithies, O., "Recombinant fragment assay for gene targeting based on the polymerase chain reaction", *Nucleic Acids Research* 16 8887–8901 (No. 18) (1988).
4. Gyllensten, U. B. and Erlich, H. A. "Methods for generating single stranded DNA by the polymerase chain reaction", WO 90/03444 (Apr. 5, 1990).
5. "Thermal Cycling with a New Twist Adds Versatility to Sequencing Automation", *Biosystems Reporter,* Issue No. 11, published by Applied Biosystems of San Jose, Calif. (February 1991).
6. Saluz, H. P. and Jost, J. P., "Genomic footprinting with Taq DNA polymerase", *Nature* 338, 277 (1989)
7. Caetan-Anollés, G., Bassam, B. J., and Gresshoff, P. M., "DNA amplification fingerprinting using very short arbitrary primers", *Biotechnology* 9, 533–557 (June 1991).
8. Saiki, R. K., "The Design and Optimization of PCR", *PCR TECHNOLOGY: Principles and Applications for DNA Amplification,* Ed. H. A. Erlich, Stockton Press (1989), at 10.
9. Innis, M. A., Myambo, K. B., Gelfand, D. H., and Brow, M. A., *Proc. Natl. Acad. Sci. (USA)* 85, 6252–6256 (1988).
10. As described in co-owned pending U.S. pat. appl. Ser. No. 07/652,427, entitled, "Methods and Apparatus for Improved Luminescence Assays" by Massey et al., filed Feb. 6, 1991.

11. PCT Appl. No. US85/02153, entitled "Luminescent Metal Chelate Labels and Means for Detection" by Bard and Whitesides.
12. PCT Appl. No. US87/00987, entitled "Electrochemiluminescent Assays" by Massey, R. J. et al.
13. PCT Appl. No. US88/03947, publication No. WO89/04302 "Electrochemiluminescent Moieties and Methods for Their Use" by Massey, R. J., Powell, M. J., Dressick, W. J., Leland, J. K., Hino, J. K., Poonian, M. S., and Della Ciana, L.
14. Della Ciana, L., Hamachi, I. and Meyer, T. J., "Synthesis of side chain derivatives of 2,2'-bipyridine", *J. Am. Chem. Soc.* 54, 1731–35 (1989).
15. Barone, A. D., Tang, J. -Y. and Caruthers, M. H., "In situ activation of bis-dialkylaminophosphines—a new method for synthesizing deoxyoligonucleotides on polymer supports", *Nucleic Acids Res.* 12, 4051–61 (1984).
16. Bannwarth, W. and Schmidt, D., *Tetrahedron Lett.* 30, 1513–16 (1989).
17. Beaucage, S. L. and Caruthers, M. H., "Deoxynucleoside phosphoramidites, a new class of key intermediates for deoxypolynucleotide synthesis", *Tetrahedron Lett.* 22, 1859–62 (1982).
18. Gray, P. W. and Goeddel, D. V., "Structure of the human immune interferon gene", *Nature* 298, 859–863 (1982).
19. Shibata, D. K., Arnheim, N. B. and Martin, J. W., "Detection of human papilloma virus in paraffin-embedded tissue using the polymerase chain reaction", *J. Exp. Med.* 167, 225–30 (1988).
20. Yanofsky, C., et. al., *Nucleic Acids Res.* 24, 6647–6668 (1981).
21. Riordan, J. R., et. al., *Science* 245, 1066–1073 (1989).
22. Yee C., Krishnan-Hewlett, I., Baker, C. C., Schlegel, R. and Howley, P. M., "Presence and Expression of Human Papillomavirus sequences in human cervical carcinoma cell lines", *Am. J. Pathol.* 119, 361–6 (1985).
23. Hall. L. O. et al., "Method and Apparatus for Conducting Electrochemiluminescent Measurements", U.S. appl. Ser. No. 744,890, filed Aug. 14, 1991 a pending continuation-in-part of U.S. appl. Ser. No. 325,459, filed Mar. 17, 1989, now allowed.
24. Zoski, G., and Woodward, S., "Apparatus for Conducting Measurements of Electrochemiluminescent Phenomena", PCT US89/04854 corresponding to pending EPO application 89912913.4, pub. Aug. 21, 1991, publication no. 0441880.

What we claim is:

1. A process for exponentially amplifying a naturally occurring target nucleic acid sequence in a sample comprising said target sequence, said process comprising the steps of:
   (a) forming a mixture of said sample and a single specified primer, such that the molar ratio of primer to target nucleic acid is at least 1000:1, and said primer (i) consists of approximately 10–40 bases; (ii) hybridizes to a first primer site at the 3' terminal of said target nucleic acid sequence; and (iii) is at least 7.5% homologous to one or more additional nucleic acid sequences 5' of said first primer site, such that the complement of at least one of said additional nucleic acid sequences serve as additional insertion site(s) for exponential amplification; and
   (b) amplifying said target nucleic acid sequence by
      (i) subjecting said mixture to conditions which cause the single primer to form a duplex product of said target nucleic acid sequence by a polymerase reaction;
      (ii) subjecting said mixture formed in step (i) to conditions which separate the duplex product into single strands; and
      (iii) repeating steps (i) and (ii) until the rate of production of duplex product is exponential and said target nucleic acid sequence has been amplified.

2. A process as recited in claim 1 wherein said primer is at least 30% complementary to one or more additional nucleic acid sequences 5' of said first primer site.

3. A process as recited in claim 1 wherein a nucleic acid sequence used in step (a) is a product of steps (b)(ii) and (b)(iii).

4. A process as recited in claim 1 wherein said steps are carried out sequentially and at a temperature above 20° C. by contacting said mixture formed in step (b) with an enzyme that forms amplification products under the conditions provided during steps (b)(ii) and (b)(iii).

5. A process as recited in claim 1 wherein step [(b)(iv)] (b)(iii) is repeated by thermal cycling between a lower temperature at which the primer initiates formation of a duplex product and a higher temperature at which the duplex product is denatured.

6. A process as recited in claim 1 wherein the primer is labeled with a detectable label or a binding substance.

7. A process as recited in claim 6 wherein said label is selected from the group consisting of a luminescent moiety, a radioactive isotope, a metal chelate, a redox active species, a nuclear magnetic resonance isotope, a dye, a marker enzyme, and a first substance able to bind a second substance, wherein said second substance is detectable.

8. A process as recited in claim 7 wherein said label is an electrochemiluminescent label.

9. A process as recited in claim 6 wherein said labeled primer is incorporated into an amplification product of said polymerase reaction.

10. A process as recited in claim 6 wherein said labeled primer is incorporated into said target nucleic acid sequence.

11. A process for exponentially amplifying a naturally occurring target nucleic acid sequence in a sample comprising said target sequence, said process comprising the steps of:
  (a) forming a mixture of said sample and a single specified primer, such that the molar ratio of primer to target nucleic acid is at least 1000:1, and said primer (i) consists of approximately 10–40 bases; (ii) selectively acts as a primer for a first primer site at the 3' terminal of said target nucleic acid sequence to generate a first primed sequence having a second priming site for said primer; and (iii) acts as a printer at said second priming site 3' of said first primer sequence and said primer is at least 7.5% complementary to said second primer site; and
  amplifying said target nucleic acid sequence by
    (i) subjecting said mixture to conditions which cause the single primer to form a duplex product of said target nucleic acid sequence by a polymerase reaction;
    (ii) subjecting said mixture formed in step (i) to conditions which separate the duplex product into single strands; and
    (iii) repeating steps (i) and (ii) until the rate of production of duplex product is exponential and said target nucleic acid sequence has been amplified.

12. A process as recited in claim 11 wherein said primer is at least 30% complementary to one or more additional nucleic acid sequences 5' of said first primer site.

13. A process as recited in claim 11 wherein a nucleic acid sequence used in step (a) is a product of steps (b)(ii) and (b)(iii).

14. A process as recited in claim 11 wherein said steps are carried out sequentially and at a temperature above 20° C. by contacting said mixture formed in step (b) with an enzyme that forms amplification products under the conditions provided during steps (b)(ii) and (b)(iii).

15. A process as recited in claim 11 wherein step (b)(iii) is repeated by thermal cycling between a lower temperature at which the primer initiates formation of a duplex product and a higher temperature at which the duplex product is denatured.
  (iii) repeating steps (i) and (ii) until the rate of production of duplex product is exponential and said target nucleic acid sequence has been amplified.

16. A process as recited in claim 11 wherein the primer is labeled with a detectable label or a binding substance.

17. A process as recited in claim 16 wherein said label is selected from the group consisting of a luminescent moiety, a radioactive isotope, a metal chelate, a redox active species, a nuclear magnetic resonance isotope, a dye, a marker enzyme, and a first substance able to bind a second substance, wherein said second substance is detectable.

18. A process as recited in claim 17 wherein said label is an electrochemiluminescent label.

19. A process as recited in claim 16 wherein said labeled primer is incorporated into an amplification product of said polymerase reaction.

20. A process as recited in claim 16 wherein said labeled primer is incorporated into said target nucleic acid sequence.

21. A method for making a primer for a single primer exponential amplification process comprising the steps of:
  (a) selecting a target nucleic acid sequence;
  (b) preparing a putative primer of approximately 10–40 base pairs designed to selectively prime or hybridize to a first primer site located at or near the 3' terminal of said target nucleic acid sequence, wherein the molar ratio of putative primer to target nucleic acid is at least 1000:1, and said putative primer is at least 7.5 % homologous to one or more additional nucleic acid sequences 5' of said first priming site, such that the complement of at least one of said additional nucleic acid sequences serve as an additional primer(s) for exponential amplification; and
  (c) conducting an amplification process to confirm that said putative primer is operative for single primer exponential amplification of said target nucleic acid sequence.

22. A method as recited in claim 21 wherein said putative primer is at least 30% homologous to one or more additional nucleic acid sequences 5' of said first primer site.

23. A method as recited in claim 21 wherein said one or more additional sequences are within 5 kb of said first primer site.

24. A method as recited in claim 21 wherein said one or more additional sequences are within 2 kb of said first primer site.

25. A method for modifying a putative primer to improve its ability to act as a primer in a single primer exponential amplification process relative to an amplification process using an unmodified putative primer, comprising the steps of:
  (a) modifying a base of said putative primer, such that said putative primer is (i) non-complementary to a corresponding base in a first primer site located at or near the 3' terminal of a target nucleic acid sequence; and (ii) complementary to a base of a second priming site on the complement of said target nucleic acid sequence situated 5' of said first primer site based on the target nucleic acid sequence; and (b) conducting a polymerase reaction to confirm that said modified putative primer is operative for single primer exponential amplification of said target nucleic acid sequence and said modified putative primer exhibits improved single primer exponential amplification relative to said unmodified putative primer.

* * * * *